United States Patent
Cocola et al.

(10) Patent No.: US 6,773,675 B2
(45) Date of Patent: Aug. 10, 2004

US006773675B2

(54) TEST TUBE FOR BIOLOGICAL ANALYSES OF ORGANIC LIQUIDS USING ELECTRO-OPTICAL EQUIPMENT

(75) Inventors: Francesco Cocola, Siena (IT); Antonio Ricci, Siena (IT)

(73) Assignee: Diesse Diagnostica Senese S.R.L., Milan (IT)

( * ) Notice: Subject to any disclaimer, the term of this patent is extended or adjusted under 35 U.S.C. 154(b) by 269 days.

(21) Appl. No.: 09/767,046

(22) Filed: Jan. 22, 2001

(65) Prior Publication Data
US 2001/0002241 A1 May 31, 2001

Related U.S. Application Data

(63) Continuation of application No. 09/194,090, filed as application No. PCT/IT97/00111 on May 13, 1997, now Pat. No. 6,190,615.

(30) Foreign Application Priority Data

May 16, 1996 (IT) .......................................... FI96A0114

(51) Int. Cl.[7] .................................................. B01L 3/00
(52) U.S. Cl. ...................... 422/102; 422/85.05; 422/99
(58) Field of Search ............................. 422/50, 63, 64, 422/68.1, 73, 82.05, 82.08, 102, 99; 436/43, 45, 47, 69, 70, 164, 165, 172; 356/335, 336, 337, 338

(56) References Cited

U.S. PATENT DOCUMENTS

| | | | | |
|---|---|---|---|---|
| 3,627,432 A | * | 12/1971 | Bergmann | 356/246 |
| 3,680,967 A | * | 8/1972 | Engelhardt | 356/246 |
| 4,319,882 A | * | 3/1982 | Sharma | 435/7.25 |
| 4,332,471 A | * | 6/1982 | Gross | 356/246 |
| 4,659,550 A | * | 4/1987 | Schildknecht | 422/73 |
| 5,571,479 A | * | 11/1996 | Koch | 422/102 |
| 5,658,532 A | * | 8/1997 | Kurosaki et al. | 422/64 |
| 5,870,182 A | * | 2/1999 | Abend et al. | 356/73 |
| 5,879,628 A | * | 3/1999 | Ridgeway et al. | 422/73 |
| 6,085,603 A | * | 7/2000 | Riekkinen | 73/864.21 |
| 6,190,615 B1 | * | 2/2001 | Cocola et al. | 422/102 |
| 6,245,570 B1 | * | 6/2001 | Grimm et al. | 436/55 |
| 6,350,412 B1 | * | 2/2002 | Williams et al. | 422/65 |
| 6,372,293 B1 | * | 4/2002 | Mathus et al. | 427/271 |
| 6,387,327 B1 | * | 5/2002 | Ricci et al. | 422/72 |
| 6,388,750 B1 | * | 5/2002 | Liu et al. | 356/436 |

\* cited by examiner

Primary Examiner—Jill Warden
Assistant Examiner—Dwayne K Handy
(74) Attorney, Agent, or Firm—McGlew and Tuttle, P.C.

(57) ABSTRACT

A test tube apparatus including a container body (1) with a cavity (3) which is essentially prismatic and has an essentially rectangular cross section, a cylindrical connecting part (5) for filling, and a flat laminar zone (7) developed as an extension of one of the walls of the cavity. Information which can be read optically, such as bar codes or the like, may be accommodated on this flat laminar zone (7).

28 Claims, 2 Drawing Sheets

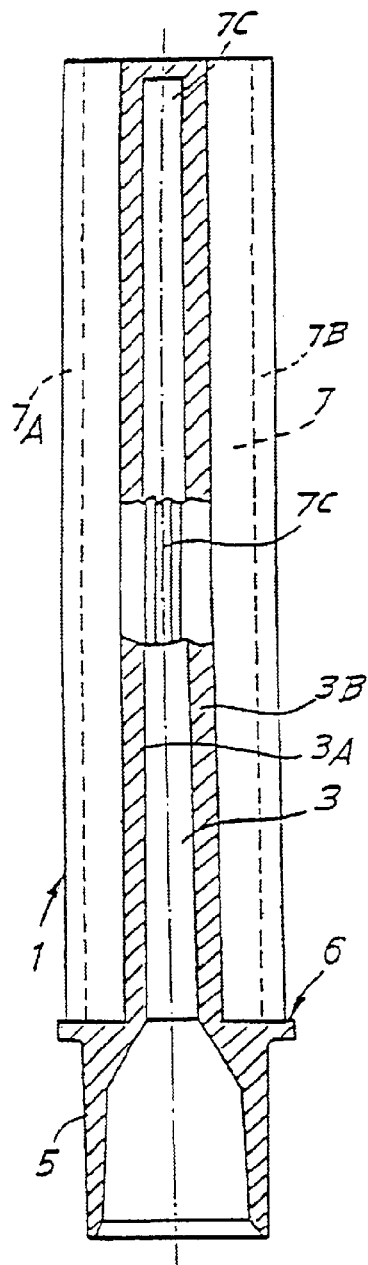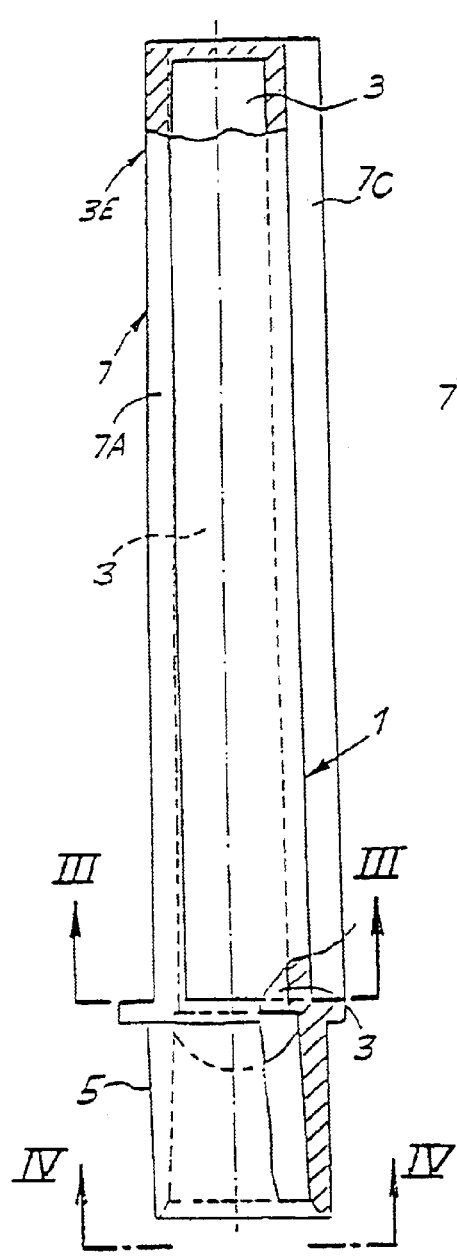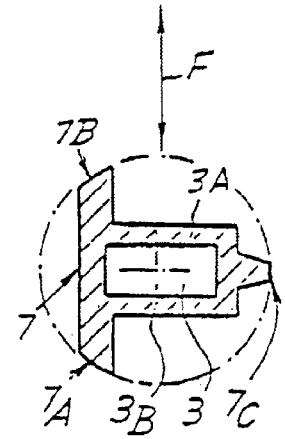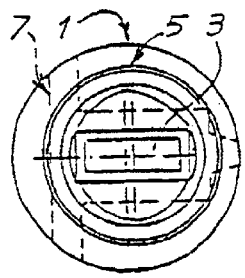

FIG. 5 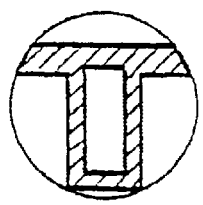 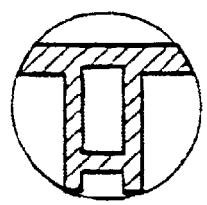 FIG. 6
FIG. 7 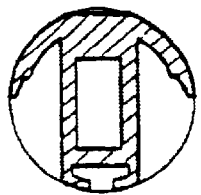 FIG. 8 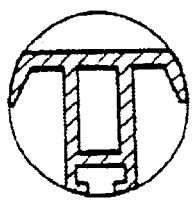 FIG. 9 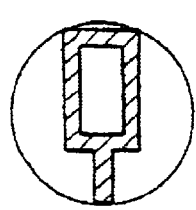
FIG. 10 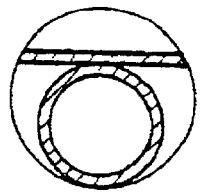 FIG. 11 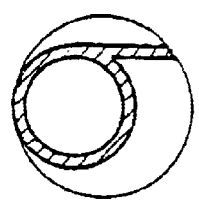 FIG. 12 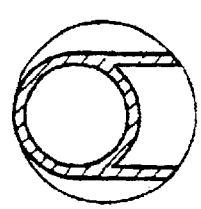
FIG. 13 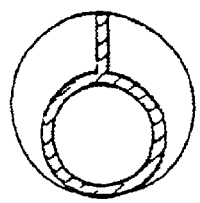 FIG. 14 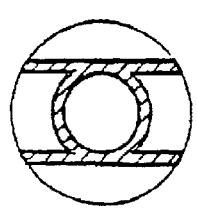 FIG. 15 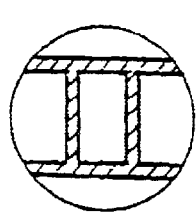

TEST TUBE FOR BIOLOGICAL ANALYSES OF ORGANIC LIQUIDS USING ELECTRO-OPTICAL EQUIPMENT

CROSS-REFERENCE TO RELATED APPLICATIONS

This is a Continuation of application Ser. No. 09/1194,090 filled Nov. 9, 1998 now U.S. Pat. No. 6,190,615, and the entire disclosure of this prior application is considered to be part of the disclosure of the accompaying application and is hereby incoporated by reference therein. Application Ser. No. 09/194,090 is the PCT National Stage of PCT Application PCT/IT97/00117/0, filled May 13, 1997, which correspondingly claims priority from Italian Patent Application F196A000114.

DESCRIPTION

1. Technical Field

The invention relates to a test tube for biological analyses of organic liquids using electro-optical equipment in general, such as photometers, for example, used for sedimentation velocity (ESR) analyses and the like.

2. Background Art

Single-use test tubes are known which are made of synthetic resin and have a tubular structure, as are other types which have a substantially prismatic cavity with a rectangular cross-section, the two larger walls of which are passed through by the rays which allow the electro-optical analysis. All these test tubes do not offer available surfaces for adopting the so-called bar codes used to read data relating to the tests and to the person whose lids being analysed; the use of labels and/or symbols and manually written information is not practical, is likely to give rise to errors and requires a considerable amount of time.

3. Objects and Disclosure of the Invention

The object of the invention is to overcome the aforementioned drawbacks and provides other objects and advantages which will become obvious from a reading of the text which follows.

Basically, the test tube in question—having a container body with a liquid-containing cavity defined by walls comprising zones located opposite one another and capable of being passed through by the rays of an optical analysing system, and a connecting part for filling and closing—according to the invention is characterized in that it comprises moreover at least one surface, which is developed so as not to interfere with said zones located opposite one another and on which-surface information which can be optically read, such as bar codes or the like, may be accommodated.

Said surface or surfaces and said container body may have, in cross-section, a form contained in a circular volume so as to be suitable for use with equipment having seats with a circular section.

According to an embodiment, the test tube may have a container body with a cavity which is substantially prismatic and has a substantially rectangular cross-section, and a cylindrical connecting part for filling, and may have at least one surface projecting from said container body. Said surface may be a portion of a cylindrical wall, also forming one of the walls of the container body. Alternatively, the said surface may be formed by a flat laminar zone projecting from the said container body. In a further alternative, the said surface is formed by a flat laminar zone developed as an extension of one of the walls of the said cavity parallel to the direction of the rays of an optical analysing system; said laminar zone may be developed symmetrically on opposite sides of the substantially prismatic cavity; the longitudinal edges of said laminar zone and an additional projection located at a distance from said edges may define a volume of the test tube contained and centred in a cylindrical housing; also the said projection may be longitudinally developed along the plane of symmetry perpendicular to said laminar zone.

According to other possible embodiments, the container body is cylindrical and has at least one surface projecting from said container body. Said surface may be formed by at least one flat laminar zone projecting from said cylindrical container body; said flat laminar zone may project tangentially from the cylindrical body or may project on opposite sides of the cylindrical body. The test tube may also comprise two flat laminar zones which are essentially parallel and spaced from one another.

Yet another test tube may comprise a container which has a substantially prismatic shape with a rectangular cross-section, and a bar code may be applied onto at least one of the walls essentially parallel to the rays of the optical analysing system.

The invention also relates to an apparatus for analyses of the type for determining the sedimentation velocity of particles in organic liquids, comprising means for receiving a plurality of test tubes and comprising optical reading means mounted on a slide designed to travel along the test tubes which are housed inside the apparatus. For use of the tests tubes described above, such an apparatus is characterized in that it comprises on said slide also means for reading data, such as a bar code, located on the carrying surface of these test tubes. The said data reading means are advantageously positioned so as to perform reading in a direction parallel to the walls of the test tube passed through by the rays of the optical analysing system. Each of the seats designed to contain the test tubes has a longitudinal opening designed to allow reading—by the reading means—of a bar code applied onto one of the surfaces of the test tube.

In any case, the test tube according to the invention offers the possibility of using an ample flat surface for receiving bar codes and other data useful for the operations for which the test tube is used.

BRIEF DESCRIPTION OF THE DRAWINGS

The invention will be more clearly understood with reference to the description and the accompanying drawing, which shows a practical non-limiting embodiment of the invention. In the drawing:

FIGS. 1 and 2 show a front and a side view respectively of a test tube according to the invention, partially sectioned;

FIGS. 3 and 4 show a section and a view of the test tube on transverse planes indicated by III—III and IV—IV in FIG. 2, respectively;

FIGS. 5 to 15 show—similarly to FIG. 3—possible variants of the test tube.

DETAILED DESCRIPTION OF PREFERRED EMBODIMENTS

With reference to FIGS. 1 to 4, the test tube 1 comprises a container body with a cavity 3 which is substantially prismatic and has a substantially rectangular cross-section and with a cylindrical connecting part 5 for filling and closing by means of a stopper not shown in the drawing. The prismatic cavity 3 has, corresponding to the long sides of its cross-section, walls 3A, 3B (FIGS. 1 and 3) which are flat and of more or less constant thickness, except for a slight variation of the internal dimension of cavity 3 for removal of the test tube from the manufacturing mould, the test tube being preferably formed using transparent plastic. These walls 3A, 3B are designed to be passed through perpendicularly, in the direction of the arrow F (FIG. 3), by the light detection rays of an electro-optical analysing system.

The test tube also an indicia wall including a flat laminar zone 7, developed as an extension of one of the walls of the said cavity 3 parallel to the direction F of the rays of the optical analysis system. This flat laminar zone 7 is capable of receiving information which can be read using reading means for example of the optical type, such as a bar code or the like. Advantageously the laminar zone 7 extends symmetrically on opposite sides of the essentially prismatic cavity.

In a preferred embodiment, the longitudinal edges 7A, 7B of said laminar zone and an additional longitudinal projection 7C located at a distance from said edges define a volume of the test tube such as to be able to center the test tube itself inside a cylindrical housing. The longitudinal projection 7C may be developed along a plane of symmetry perpendicular to said laminar zone 7. All this makes it possible to achieve effective centering of the test tube in the seats provided in the analysing equipment.

In any case the test tube offers the possibility of using an ample flat surface 7 for receiving bar codes and/or other data useful for the operations for which the test tube is used.

FIGS. 5 to 15 show cross-sections of further possible embodiments of test tubes which have requirements equivalent to those of the test tube already described. These test tubes have at least one surface capable of receiving the information, such as the surface 7, and a volume contained within a circular profile (viewed in cross-section); moreover, the containing space of the body of the test tube may be analysed by a beam of rays which pass through it, being defined with flat or also curved walls, as far as a circular cross-section.

It is understood that the drawing shows only an example provided by way of a pratical demonstration of the invention, it being possible to vary the forms and arrangements thereof without thus departing from the scope of the idea underlying the invention itself. The presence of any reference numbers in the accompanying claims has the purpose of facilitating reading of the claims with reference to the description and to the drawing, and does not limit the scope of protection represented by the claims.

What is claimed:

1. A test tube apparatus comprising:
a container body defining a cavity capable of holding a sample, said container body having a longitudinal axis and two substantially flat and parallel opposite walls extending along said longitudinal axis, said opposite wails being formed of a material and a shape for passing detection rays through said opposite walls and through said cavity;
an indicia wall connected to said container body and extending longitudinally along said container body, said indicia will being spaced from said opposite walls and spaced from the detection rays, said indicia wall being receivable of optically readable information and being integral with said container body.

2. Test tube apparatus according to claim 1, wherein:
said container body has a substantially circular cross-section.

3. Test tube apparatus according to claim 1, wherein:
said cavity is essentially prismatic and has an essentially rectangular cross-section;
a cylindrical connecting part for filling projects from said container body.

4. Test tube apparatus according to Claim 1, wherein:
said indicia wall also forms a wall of the container body.

5. Test tube apparatus according to claim 1, wherein:
said indicia wall is formed by a flat laminar zone projecting from said container body.

6. Test tube apparatus according to claim 1, wherein;
said indicia wall is formed by a flat laminar zone developed as an extension of a wall of said cavity parallel to a direction of said detection rays of an optical analyzing system.

7. Test tube apparatus according to Claim 6, wherein:
said laminar zone extends symmetrically on opposite sides of said cavity, said cavity having a substantially prismatic shape.

8. Test tube apparatus according to claim 6, wherein:
longitudinal edges of said laminar zone and an additional projection located at a distance from said edges define a volume of the test tube contained and centered in a cylindrical housing.

9. Test tube apparatus according to claim 8, wherein:
said additional projection is longitudinal and is developed along a plane of symmetry perpendicular to said laminar zone.

10. Test tube apparatus according to claim 1, wherein:
said indicia wall projects tangentially from the container body.

11. Test tube apparatus according to claim 10, wherein:
said indicia wall projects on opposite sides of the container body.

12. Test tube apparatus according to claim 1, wherein:
two of said indicia walls are provided on said container body and are substantially parallel and spaced from one another.

13. Test tube apparatus according to claim 1, wherein:
said container body has an essentially prismatic shape and a rectangular cross-section;
a bar code is applied onto at least one of the walls substantially parallel to the detection rays.

14. The apparatus in accordance with claim 1, wherein:
said indicia wall has a substantially flat surface substantially parallel with said longitudinal axis of said container body.

15. The apparatus in accordance with claim 1, wherein:
said indicia wall has a substantially flat surface substantially parallel to the detection rays.

16. The apparatus in accordance with claim 1, wherein:
said indicia wall is non-intersecting of the detection rays, and said indicia wall is in a plane substantially parallel with said longitudinal axis of said container body, said indicia wall has a substantially flat surface substantially parallel to the detection rays.

17. The apparatus in accordance with claim 14, wherein:
said substantially flat surface has a width larger than a distance between said opposite walls.

18. The apparatus in accordance with claim 1, wherein:
said container body and said indicia wall form longitudinal edges for centering and supporting said container body in a seat.

19. The apparatus in accordance with claim 5, wherein:

said flat laminar zone has a longitudinal edge arranged substantially parallel to said longitudinal axis of said container body and arranged adjacent to said container body.

20. A test tube apparatus comprising:

a cylindrical container body defining a cavity capable of holding a sample, said container body having a longitudinal axis and opposite walls extending along said longitudinal axis, said opposite walls being formed of a material and a shape for passing rays through said opposite walls and through said cavity;

an indicia wall connected to said container body and extending longitudinally along said container body, said indicia wall being spaced from said opposite walls spaced from the detection rays, said indicia wall being receivable of optically readable information, said indicia wall being formed by a flat laminar zone projecting from said container body, said flat luminar zone having a longitudinal edge arranged substantially parallel to said longitudinal axis of said container body and said indicia wall being integral with the container body.

21. A test tube apparatus comprising:

a container body defining a cavity capable of holding a sample, said container body having a logitudinal axis and two substantially flat and parallel opposite walls extending along said longitudinal axis, said opposite walls being formed of a material and a shape for passing detection rays through said opposite walls and through said cavity;

an indicia wall connected to said container body and extending longitudinally along said container body, said indicia wall being receivable of optically readable information;

a cylindrical connecting part for filling said cavity projects from said container body.

22. A test tube apparatus comprising:

a cylindrical container body defining a cavity capable of holding a sample, said container body having a longitudinal axis and opposite walls extending along said longitudinal axis, said opposite walls being formed of a material and a shape for passing detection rays through said opposite wails and through said cavity, said cavity being essentially prismatic and having an essentially rectangular cross-section;

an indicia wall connected to said container body and extending longitudinally along said container body, said indicia wall being spaced from said opposite walls and spaced from the detection rays, said indicia wall being receivable of optically readable information; and a cylindrical connecting part for filling projecting from said container body.

23. A test tube apparatus comprising:

a cylindrical container body defining a cavity capable of holding a sample, said container body having a longitudinal axis and opposite walls extending along said longitudinal axis, said opposite walls being formed of a material and a shape for passing detection rays through said opposite walls and through said cavity;

an indicia walls connected to said container body and extending longitudinally along said container body, said indicia wall being spaced from said opposite walls and spaced from the detection rays, said indicia walls being receivable of optically readable information, said indicia wall also forming a wall of the container body.

24. A teat tube apparatus comprising:

a cylindrical container body defining a cavity capable of holding a sample, said container body having a longitudinal axis and opposite walls extending along said longitudinal axis, said opposite walls being formed of a material and a shape for passing detection rays through said opposite walls and through said cavity; and two indicia walls connected to said container body and extending longitudinally along said container body, said indicia walls being spaced from said opposite walls and spaced from the detection rays, said indicia wall being receivable of optically readable information, said two indicia walls being provided on said container body and being substantially parallel and spaced from one another.

25. A test tube apparatus comprising:

a cylindrical container body defining a cavity capable of holding a sample, said container body having a longitudinal axis and opposite walls extending along said longitudinal axis, said opposite walls being formed of a matedal and a shape for passing detection rays through said opposite walls and through said cavity, said container body having an essentially prismatic shape and a rectangular cross-section;

an indicia wall connected to said container body and extending longitudinally along said container body, said indicia wail being spaced from said opposite walls and spaced from the detection rays, said indicia wall being receivable of optically readable information; and a bar code applied onto at least one of the walls substantially parallel to the detection rays.

26. A test tube apparatus comprising.

a cylindrical container body defining a cavity capable of holding a sample, said container body having a longitudinal axis and opposite walls extending along said longitudinal axis, said opposite walls being formed of a material and a shape for passing detection rays through said opposite wails and through said cavity; and an indicia wail connected to said container body and extending longitudinally along said container body, said indicia wall being spaced from said opposite walls and spaced from the detection rays, said indicia wall being receivable of optically readable information, said indicia wall being formed by a flat laminar zone developed as an extension of a wall of said cavity, said laminar zone extending symmetrically on opposite sides of said cavity, said cavity having a substantially prismatic shape.

27. A test tube apparatus comprising:

a cylindrical container body defining a cavity capable of holding a sample, said container body having a longitudinal axis and opposite walls extending along said longitudinal axis, said opposite walls being formed of a material and a shape for passing detection rays through said opposite walls and through said cavity; and an indicia wall connected to said container body and extending longitudinally along said container body, said indicia wall being spaced from said opposite walls and spaced from the detection rays, said indicia wall being receivable of optically readable information, said indicia wall is formed by a flat laminar zone developed as an extension of a wall of said cavity, longitudinal edges of said laminar zone and an additional projection located at a distance from said edges defining a volume of the test tube contained and centered in a cylindrical housing.

28. A test tube apparatus comprising:

a container body defining a cavity capable of holding a sample, said container body having a longitudinal axis and two substantially flat and parallel opposite walls extending along said longitudinal axis, said opposite walls being formed of a material and a shape for passing detection rays through said opposite walls and through said cavity;

an indicia wall connected to said container body and extending longitudinally along said container body, said indicia wall being spaced from said opposite walls and spaced from the detection rays, said indicia wall being receivable of optically readable information, said indicia wall is formed by a flat laminar zone developed as an extension of a wall of said cavity parallel to a direction of said detection rays of an optical analyzing system, said laminar zone extends symmetrically on opposite sides of said cavity, said cavity having a substantially prismatic shape.

* * * * *